United States Patent
Ziegler et al.

(10) Patent No.: US 6,388,752 B1
(45) Date of Patent: May 14, 2002

(54) OPTICAL MEASUREMENT SYSTEM FOR DETERMINATION OF TRANSMITTED AND SCATTERED RADIATION

(75) Inventors: Werner Ziegler; Ewald Jöbstl; Manfred Strohmeier, all of Graz (AT)

(73) Assignee: F. Hoffmann-La Roche AG, Basel (CH)

(*) Notice: Subject to any disclaimer, the term of this patent is extended or adjusted under 35 U.S.C. 154(b) by 0 days.

(21) Appl. No.: 09/572,594

(22) Filed: May 17, 2000

(30) Foreign Application Priority Data

May 20, 1999 (AT) ................................. 900/99

(51) Int. Cl.⁷ .................. G01N 21/00; G01N 33/48
(52) U.S. Cl. .................. 356/436; 356/39; 356/440; 356/342
(58) Field of Search ................. 356/436, 440, 356/338, 342, 39–42

(56) References Cited

U.S. PATENT DOCUMENTS 4,745,279 A    5/1988    Karkar et al.
5,241,368 A  * 8/1993    Ponstingl et al. ........... 356/436
5,781,284 A  * 7/1998    Infante ........................ 356/436
5,828,458 A   10/1998    Taylor et al.

FOREIGN PATENT DOCUMENTS

| | | |
|---|---|---|
| DE | 2625088 | 12/1977 |
| EP | 0575712 | 12/1993 |
| EP | 0720013 | 7/1996 |
| EP | 0800074 | 10/1997 |
| WO | 9944043 | 9/1999 |

* cited by examiner

*Primary Examiner*—Frank G. Font
*Assistant Examiner*—Amanda Merlino
(74) *Attorney, Agent, or Firm*—Dykema Gossett PLLC

(57) ABSTRACT

An optical measurement system for determining transmitted radiation and scattered radiation in a liquid sample contained in a capillary tube and subject to measurement radiation, is provided with a first detector picking up transmitted radiation, which is positioned close to or on the axis of the beam of measurement radiation. There is further provided a second detector for picking up scattered radiation, which is positioned at a distance from the first detector in the direction of the capillary axis. The two detectors lie on different sides of a plane which contains the capillary axis and is normal to the axis of the measurement radiation.

7 Claims, 4 Drawing Sheets

OPTICAL MEASUREMENT SYSTEM FOR DETERMINATION OF TRANSMITTED AND SCATTERED RADIATION

BACKGROUND OF THE INVENTION

The present invention relates to an optical measurement system for the determination of transmitted radiation and scattered radiation in a liquid sample contained in a capillary tube and subject to measurement radiation, where the axis of the beam of measurement radiation is essentially at a right angle to the axis of the capillary tube, and where a first detector which is used for picking up transmitted radiation, is positioned in an area near the axis of the beam of measurement radiation, and where a second detector which is used for picking up scattered radiation, is placed at a certain distance from the first detector in the direction of the axis of the capillary tube.

Such measurement systems are predominantely used for testing liquid media containing absorbent scattering particles, e.g., whole blood samples and other organic or inorganic liquids, but also liquid samples in environmental technology, such as waste-water samples.

The determination of the concentration of substances in such liquids may be effected by measuring absorption at various wavelengths in a transmission configuration and in a scattered light configuration, where the measured intensities of transmitted and scattered light together with calibrating data from known samples and zero values (measured values when the capillary is filled with pure water) permit the substance concentrations to be determined.

DESCRIPTION OF THE PRIOR ART

From EP 0 800 074 A1 a device is known for the determination of the concentration of derivatives of hemoglobin in an undiluted, unhemolised whole blood sample. The whole blood sample contained in a test tube is subjected to measurement radiation that is made up of at least n monochromatic, narrowband components of various wavelengths. A first detector unit is positioned on the axis of the primary beam (transmission geometry). The detector has a relatively small beam entry area and essentially picks up radiation from the central beam. In a second measurement position, at a certain angle with the axis of the primary beam, a second detector unit is placed for picking up scattered radiation. Both detector units are connected via signal lines to an evaluation unit, where values for the hemoglobin derivatives are computed by means of a stored calibration matrix.

From EP 0 720 013 A2 a method and device for the optical determination of blood parameters is known, where one embodiment shows a flow cell in a housing, which takes up the blood sample. Measurement radiation from a lightsource is introduced at a right angle to the axis of the flow cell, and on the other side of the cell a first detector is positoned in transmission configuration, while further detectors are provided in scatter configuration at various distances from the first. The measuring cell of the embodiment described may be directly included in an extracorporeal blood circuit and thus be used in the optimisation of a dialysis process.

Furthermore, in U.S. Pat. No. 4,745,279 a device for hematocrit-measurement in blood has been described, where infrared radiation is radiated into a transparent cell through which blood flows. A first detector situated at the bottom of the cell picks up diffusely scattered light from the sample, which presents a measure for oxygen saturation. A second detector placed on a sidewall of the cell is used for measuring hematocrit. Excitation light for both detectors is provided by two different lightsources (LEDs), which are placed pairwise in the respective regions of the detectors. A third lightsource, which does not interact with the sample, and a third detector are used to create a reference signal.

A measurement system of the kind described above is known from EP 0 575 712 A2, which may be used to simultaneously determine the hematocrit value and one other quantity, for instance sodium concentration, directly in vitro or in an extra-corporeal blood circulation. The collimated beam from a lightsource enters a measuring chamber containing the blood sample, at a right angle to the flow direction of the sample. For absorption measurement two photodetectors are employed, the first being oriented in the direction of the incident light (transmitted radiation), while the second is positioned at a distance from this central direction (scattered radiation). The radiation components picked up by this second detector are strongly influenced by the sodium concentration, thus permitting its quantitative determination.

Since the intensity of transmitted radiation is by far greater than that of scattered radiation (by a factor 100), a disadvantageous influence on the scattered light detector by the measurement radiation cannot be avoided in the known measurement systems. At least part of the primary measurement radiation may enter the scattered light detector via scattering or reflection processes outside the sample or directly and may thus invalidate measurement results.

SUMMARY OF THE INVENTION

It is the object of the present invention to further develop a measuring system as described above in such a way that a relevant measurement signal which is not influenced by primary radiation, may be picked up by the scattered light detector.

The invention attains this by positioning the first detector and the second detector on different sides of a plane which contains the capillary axis and is at a right angle with the axis of the measurement beam. Scattered radiation is thus measured in a back scatter position, which is novel compared with the state of the art and ensures that an influence of the primary measurement radiation on the scattered light detector is avoided simply by the geometry of the set up. By this means the intensity for the zero value measurement (capillary filled with pure water) may be kept very low, which will result in a large analytic measurement range. When a real sample is measured the measurement radiation interacts with the scattering particles of the sample and is partly absorbed and partly scattered independently of direction. Part of the scattered light propagates in the direction of the second detector (the scattered light detector), another part arrives at the wall of the capillary or enters this wall, which acts as a light guide and again introduces a part of this light into the sample, where it is subject to further scattering. Thus the measurement radiation may propagate over a relatively long interaction zone in the direction of the scattered light detector, where it is picked up as scattered radiation by the second detector placed at a right angle to the capillary axis. In a preferred variant of the invention the optical axis of the second detector is oriented essentially parallel to the axis of the beam of measurement radiation. Although even considerable deviations from the parallel alignment (+/−80°) will still produce useable results, as long as the scattered light detector is positioned in a back-scatter geometry, the best results will of course be obtained in the 0°-position (see embodiment in FIG. 4).

Optical conductivity of the capillary wall is provided in a variant of the invention by an optically thinner medium (e.g. air) on the outside of the capillary wall. If the capillary is placed in the bore of a measurement block, the invention prescribes that between the input region of the measurement radiation and the output region of the scattered radiation be placed at least one optical separating element, which covers the annular gap between the capillary and the wall of the bore. This will prevent parts of the measurement radiation from reaching the second detector by reflexion or mirror effects or scattering in air on the outside of the capillary.

It is of particular advantage in this respect to configure the optical separating element as an 0-ring or as a ring with square cross-section which will center the capillary in the bore of the measurement block.

It has furthermore been found that the signal quality of the scattered light detector can be improved if the bore of the measurement block has a diffusely reflecting surface at least between the input region of the measurement radiation and the output region of the scattered radiation.

In another advantageous variant of the invention it is provided that the exterior wall of the capillary, except the input region of the measurement radiation and the output region of the scattered radiation, is mirror-coated or coated with a dichroic layer.

BRIEF DESCRIPTION OF THE FIGURES

The invention will now be described in more detail with reference to partly schematical drawings.

DETAILED DESCRIPTION OF THE PREFERRED EMBODIMENTS

Figure 1:
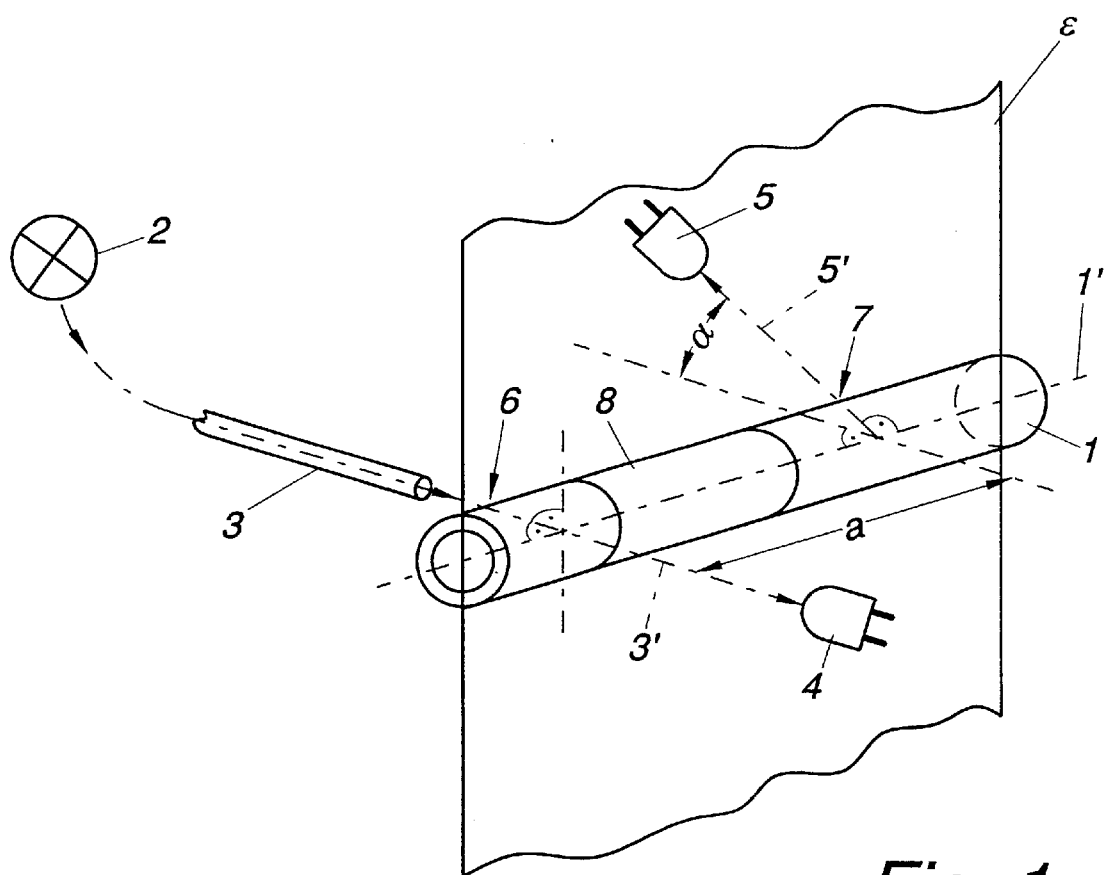
FIG. 1 is a schematical representation of a measurement system according to the invention for the determination of transmitted and scattered radiation in a liquid sample.

The optical measurement system shown in FIG. 1 comprises a capillary with an axis $1'$, which contains the sample to be measured or through which the sample flows when the capillary forms part of an extracorporeal circuit. Measurement radiation departing from a lightsource 2 via an optical fiber 3 is radiated into the capillary 1 in radial direction, such that the axis $3'$ of the measurement beam is essentially at a right angle to the axis $1'$ of the capillary 1. On the opposite side of the capillary a first detector 4 is placed in the area of the axis $3'$ of the measurement beam to pick up transmitted radiation. A second detector 5 for picking up scattered radiation is placed at a distance a in the direction of the capillary axis $1'$, the first detector 4 and the second detector 5 being placed on different sides of a plane $\epsilon$ which contains the capillary axis $1'$ and stands at a right angle to the axis $3'$ of the beam of measurement radiation. The optical axis $5'$ of the second detector 5 also is essentially normal to the capillary axis $1'$, but may form an angle $\alpha$ with the axis $3'$ of the measurement radiation, which may be in a range of +/−80°. Preferred in this respect are embodiments in which the optical axis $5'$ of the second detector 5 is essentially parallel to the axis $3'$ of the measurement radiation.

In the embodiment shown in FIG. 1 the exterior wall of the capillary 1 is provided with a mirror coating 8 or a dichroic layer with the exception of the input region 6 of the measurement radiation and the output region 7 of the scattered radiation. Aluminum may for instance be vapourised onto the capillary, annular areas of approx. 2 mm width for the input and output regions 6 and 7 remaining mirror-free.

Figure 3:
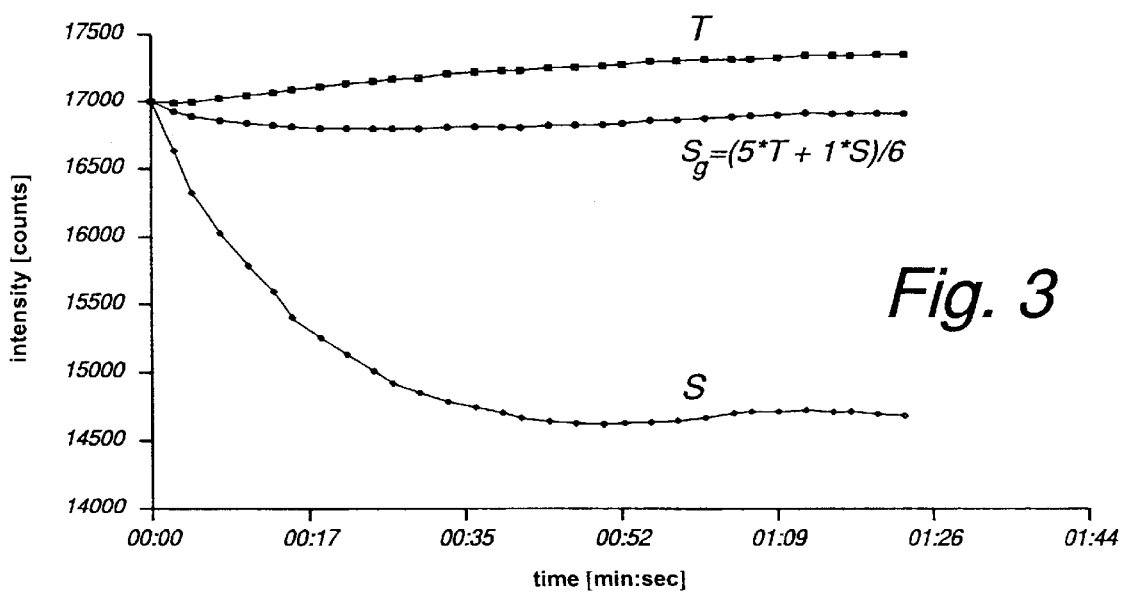
FIG. 3 is a diagram which shows the change in intensity over time.

In the measurement process measurement radiation is radiated into the capillary 1 at a right angle with a defined aperture in such a way that the passing of radiation beyond the exterior contour of the capillary is avoided. The radiated light interacts with the absorbing scattering particles in the sample, i.e., it is partly absorbed and partly scattered independently of direction. Part of the measurement radiation directly arrives at the detector 4 which picks up transmitted radiation. Part of the scattered light propagates in the sample where those parts which enter the wall of the capillary 1 are reflected back into the sample either by total reflexion (as shown in the embodiment of FIG. 3) or due to the mirror coating 8 of the exterior surface. Along the distance a a relatively extended zone of interaction develops within which multiple scattering may occur. The scattered radiation is then picked up by the detector 5 which is also postioned at a right angle to the capillary axis $1'$ and is provided with a defined aperture.

Figure 2:
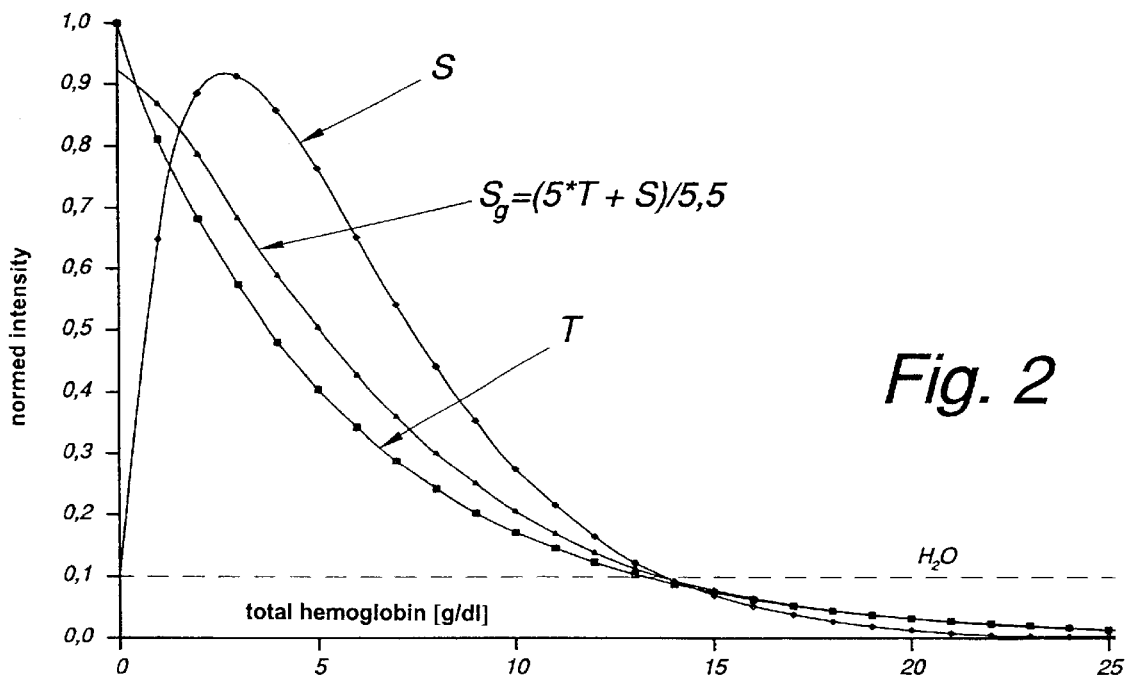
FIG. 2 shows a diagram of the intensity of transmitted and scattered light as a function of the substance concentration in the sample.

FIG. 2 shows normed intensity T (transmission detector 4) respectively S (scatter detector 5) plotted against the concentration of the scattering medium in the sample (for instance hemoglobin concentration in whole blood in g/dl). The zero value of the measurement system, i.e., when the capillary is filled with water, is indicated by $H_2O$; $S_g$ refers to a signal which is a weighted sum of the intensities T and S.

The transmitted light detector 4 delivers a signal which, as a function of concentration, is represented by a continuous monotonously decreasing curve T analogous to Lambert-Beer's law. The scattered light detector 5 on the other hand delivers a measurement curve S resulting from a superposition of diffuse scattering and absorption. With increasing concentration of the substances in the sample the signal intensity increases with a maximum at approximately 2–3 g/dl and thereafter falls continuously with increasing concentration.

A great number of samples make measuring difficult as the scattering particles tend to sediment during the measurement process if the sample cannot be kept in motion sufficiently. This will cause a drift in the detected signals and may lead to errors of measurement.

The system of the invention is particularly well suited to overcome this kind of measurement problem.

If the scattering particles sediment, the concentration of the sample becomes inhomogeneous over the cross-section of the capillary. This will result in an increase of the signal T of the transmitted light detector, since mean absorption decreases due to separation and because of the nonlinear characteristic.

In contrast to this the measurement signal of the scattered light detector will decrease because of a lack of scattering particles in the "less dense" part of the sample and an absorption increase in the "denser" part.

If both signals, i.e., the one from the scatter detector and the other one from the transmission detector, are combined in a suitable way, the individual errors will compensate each other to the first order, resulting in a measurement signal which is largely free of drift during the measurement time. Integration time may thus be increased and the signal/noise ratio may be improved.

The two measurement signals T and S may for instance be combined to form a weighted-sum signal $S_g$. As can be seen from FIG. 3 the weighted-sum signal (e.g. from human blood with tHb of 5 g/dl) remains constant in a measurement window from approx. 20s to 50s, which will permit driftfree measurement at multiple wavelengths.

A further advantage of this arrangement is given by the fact that by suitably chosen weights of the signals T and S a sum signal may be obtained which has varying sensitivity over the range of concentrations to be measured. This will be of particular advantage in measurements of whole blood. In blood samples with very low tHb values (3<tHb<5 g/dl) increased measurement accuracy is desirable in order to provide a sound basis for treatment decisions, i.e., whether the patient should receive an infusion or a transfusion. As can be seen from FIG. 2 the combination of the signals may significantly enlarge the range of measurement in the direction of low concentrations without encountering the problem of signal ambiguity (due to the maximum of the scatter signal S).

Another advantage of the system according to the invention results from the fact that the transmission signal and the scatter signal show a defined relationship of the respective curves which is specific for a given type of sample (i.e., human blood). It is thus possible to identify the type of sample (for instance bovine blood) and to discriminate between types. Although human and bovine blood have very similar absorption characteristics, such samples will differ in the size of red blood cells (i.e. scattering centers). This will alter the light propagation mechanism in the scatter geometry relative to that in the transmission geometry in such a way that samples of different type may be clearly distinguished. Interfering substances, such as dyes which should not be present in the sample, can be identified, if they alter the functional dependence of the curves sufficiently.

Figure 4:
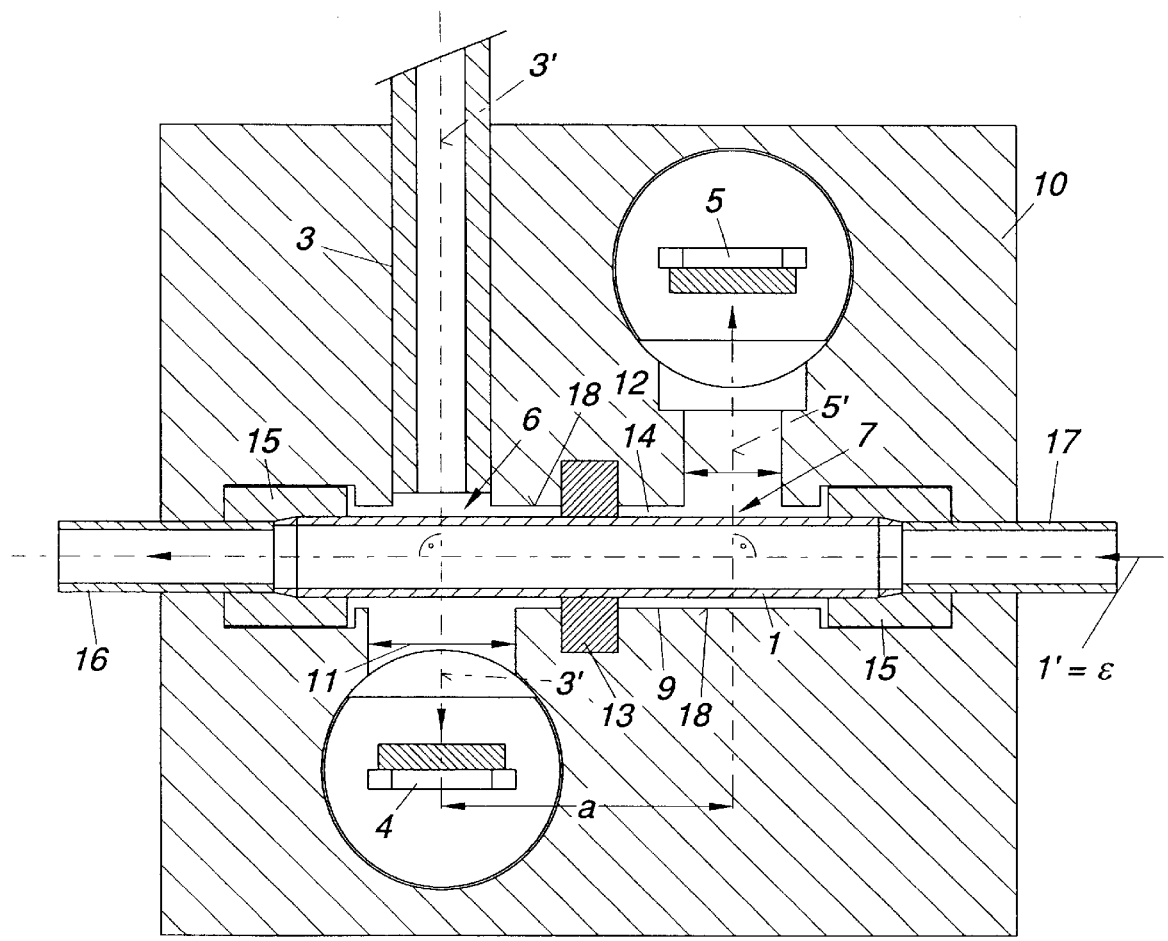
FIG. 4 shows a preferred embodiment of the invention.

In the preferred embodiment shown in FIG. 4 the optical axis 5' of the second detector 5 is parallel to the axis 3' of the measurement radiation. In this figure the plane ε is normal to the plane of the picture and coincides with the axis of the capillary 1'. In this embodiment the capillary 1 is placed in the bore 9 of a measurementblock 10, which further contains the optical fiber 3, the aperture 11 for the transmission detector 4 and the aperture 12 for the scatter detector 5. An optical separating element 13 is placed between the input region 6 for the measurement radiation and the output region 7 for the scattered radiation, which closes the annular gap 14 between the capillary 1 and the bore 9. The optical separating element 13 may for instance be an O-ring of black rubber which is held in a groove of the bore 9. The separating element will efficiently block the coupling of stray light into the scattered light detector 5 and at same time will center the capillary 1 in the bore 9. The capillary 1 may furthermore be fixed in place by sealing elements 15, which connect the capillary on the input and output side with feeding and draining tubes 16 and 17 for the sample.

In the embodiment with an air gap 14 as shown in FIG. 4 the efficiency of the process may be improved by providing that the bore 9 of the measurement block 10 have a diffusely reflecting surface 18 at least between the input area 6 and the output area 7. It has been found that this kind of surface treatment yields best results as it has no preferred direction for reflection back into the sample and is thus less sensitive to local inhomogeneities than mirror-coated surfaces.

In order to determine a zero value for the measurement system, which may be used in the compensation of intensity changes of the measurement radiation and of changes in the optical path, two measurements are performed in which the capillary is filled with water. In this case the first detector 4 in transmission geometry will record changes in the intensity of the lightsource and losses of the measurement radiation upon entry into the capillary 1. For the second detector 5 in scatter geometry the zero value measurements will give additional information regarding changes inside the capillary, such as the formation of deposits or buildup of dirt, and regarding the output region of the capillary. Both zero value measurements should preferably be made synchronously in order to compensate for intensity fluctuations of the lightsource during reference measurement.

By suitable choice of the optically relevant parameters such as diameter of the capillary, wall thickness of the capillary, distance a between input region 6 and output region 7 (interaction zone), optical properties of the bore 9, aperture of the input and output geometry, etc., the shape of the curve of the measurement function of the scattered light detector 5 may be adapted to specific requirements. The position of the maximum of the curve (see FIG. 2) may for instance be chosen such that it lies below the expected minimal concentration of the samples to be measured, thus avoiding ambiguity of the measurement results. The mean slope or the slope function over the measurement range of interest may also be adjusted and optimised within certain limits.

For the measurement of tHb and SO2 in a whole blood sample the capillary typically has an interior diameter of 1.1 to 1.6 mm and the distance a between input region 6 and output region 7 is 4 to 10 mm. The optical fiber has a core diameter of about 1 mm, the size of the apertures 11 and 12 is 1.5 to 2.5 mm.

A further advantage of the measurement function shown in FIG. 2 or rather its adaptation to specific requirements lies in the fact that the maximal intensity of scattered radiation is attained at a defined minimal sample concentration and that the total dynamical range of the measurement system may be utilised for the total range of concentration, which also means optimal utilisation of the resolution obtainable by the detection system. This will be of particular advantage if the medium to be measured is strongly absorbing, may not be diluted or can be introduced into a sufficiently thin cuvette only with difficulty due to reasons of flow dynamics, which is the case mainly for biological fluids and especially for whole blood.

Figure 5:
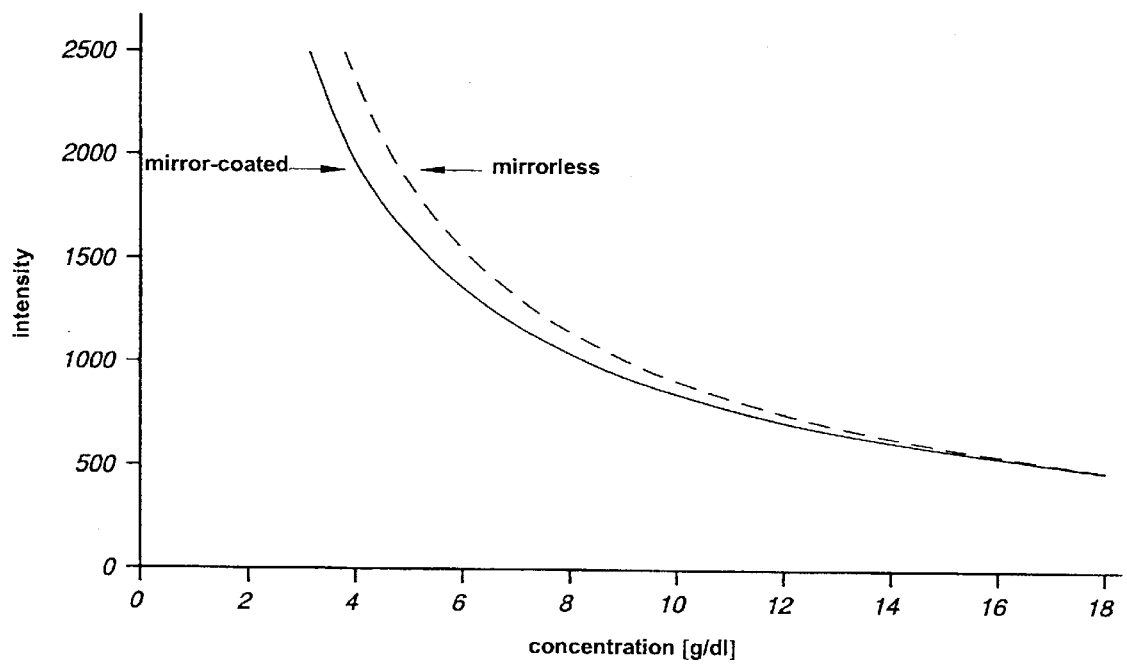
FIG. 5 (transmitted radiation)
Figure 6:
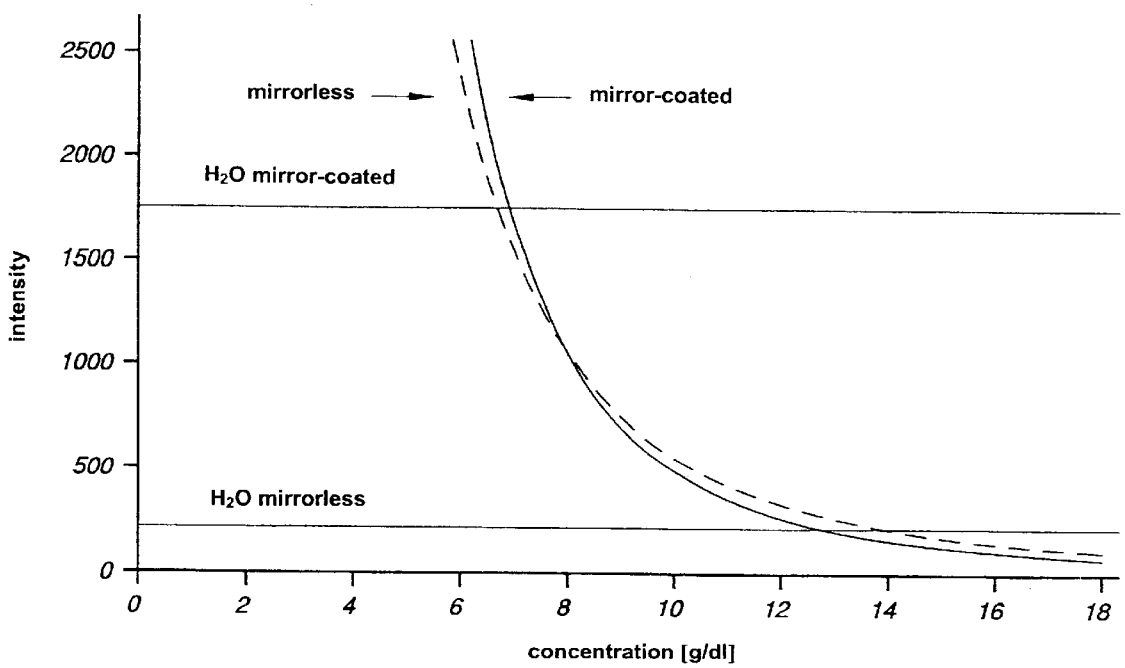
FIG. 6 (scattered radiation) shows intensity as a function of the substance concentration in the sample.

In FIG. 5 and 6 intensity is plotted on the ordinate against concentration in g/dl on the abscissa. FIG. 5 shows the intensity curve of transmitted radiation (detector 4) for a capillary with air gap (mirrorless) and for a mirror-coated capillary. FIG. 6 shows the intensity curve (amplified by a factor 100) of the scattered light detector (detector 5) for both variants (mirror-coated and mirrorless), the zero value for a water filled capillary being also shown for both variants ($H_2O$ mirror-coated resp. $H_2O$ mirrorless).

What is claimed is:

1. An optical measurement system for determination of transmitted and scattered radiation of a liquid sample contained in a capillary and subject to measurement radiation, said measurement radiation having an optical axis being essentially at a right angle to a central axis of said capillary, comprising a first detector being provided for picking up transmitted radiation, which is positioned close to or on said optical axis of said measurement radiation, and a second detector defining an optical axis and being provided for picking up scattered radiation, which is placed at a distance from said first detector in a direction of said central capillary axis, wherein said first detector and said second detector are positioned on different sides of a plane $\epsilon$, which contains said central capillary axis and is at a right angle with said optical axis of said measurement radiation wherein said capillary is placed in a bore of a measurement block and is provided with at least one optical separating element between an input region of said measurement radiation and an output region of said scattered radiation, wherein said separating element covers an annular gap between said capillary and the wall of said bore.

2. A measurement system as in claim 1, wherein said optical axis of said second detector is essentially parallel to said axis of said measurement radiation.

3. A measurement system as in claim 1, wherein said optical separating element is configured as an O-ring, centring said capillary in said bore of said measurement block.

4. A measurement system as in claim 1, wherein said optical separating element is configured as a ring with square cross-section, centring said capillary in said bore of said measurement block.

5. A measurement system as in claim 1, wherein said bore of said measurement block has a diffusely reflecting surface at least between said input region of said measurement radiation and said output region of said scattered radiation.

6. A measurement system as in claim 1, wherein the exterior wall of said capillary, except said input region of said measurement radiation and said output region of said scattered radiation, is mirror-coated.

7. A measurement system as in claim 1, wherein the exterior wall of said capillary, except said input region of said measurement radiation and said output region of said scattered radiation, is coated with a dichroic layer.

* * * * *